United States Patent [19]
Budowsky

[11] Patent Number: 6,136,586
[45] Date of Patent: *Oct. 24, 2000

[54] METHODS FOR THE SELECTIVE MODIFICATION OF VIRAL NUCLEIC ACIDS

[75] Inventor: Edward I. Budowsky, Brookline, Mass.

[73] Assignee: VI Technologies, Inc., Watertown, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/855,378

[22] Filed: May 13, 1997

Related U.S. Application Data

[63] Continuation-in-part of application No. 08/705,045, Aug. 29, 1996, abandoned, which is a continuation-in-part of application No. 08/521,245, Aug. 29, 1995.

[51] Int. Cl.$^7$ .............................. C12N 7/06; A01N 1/02
[52] U.S. Cl. ................................ 435/238; 435/2
[58] Field of Search .................................. 435/238, 236, 435/2

[56] References Cited

U.S. PATENT DOCUMENTS

| | | | |
|---|---|---|---|
| 3,492,289 | 1/1970 | Symm et al. | 260/239 |
| 4,036,952 | 7/1977 | Bauer et al. | |
| 4,058,599 | 11/1977 | Bauer et al. | |
| 4,841,023 | 6/1989 | Horowitz | 530/351 |
| 5,000,951 | 3/1991 | Bass et al. | 424/89 |
| 5,055,485 | 10/1991 | Geacintov et al. | 514/449 |
| 5,120,649 | 6/1992 | Horowitz et al. | 435/173 |
| 5,232,844 | 8/1993 | Horowitz et al. | 435/173.1 |
| 5,374,424 | 12/1994 | Kelsey et al. | 424/202.1 |
| 5,559,250 | 9/1996 | Cook et al. | |

FOREIGN PATENT DOCUMENTS

| | | |
|---|---|---|
| 0612532 A2 | 8/1994 | European Pat. Off. |
| 101400 | 4/1992 | Romania |
| 1768636 | 10/1992 | U.S.S.R. |
| 178636 A1 | 10/1992 | U.S.S.R. |
| 594771 | 7/1993 | U.S.S.R. |
| 594771 A1 | 7/1993 | U.S.S.R. |
| WO 92/03157 | 3/1992 | WIPO |
| WO 92/18161 | 10/1992 | WIPO |
| WO 96/39818 | 12/1996 | WIPO |

OTHER PUBLICATIONS

Murphy, "Virus Taxonomy", pp. 15–57 in Fields et al., Fields Virology, Lippincott–Raven, Philadelphia, 1996.
Creech et al., "Antitumor and Mutagenic Properties of a Variety of Heterocyclic Nitrogen and Sulfur Mustards," Medicinal Chemistry, 15: 739–746, 1972.
International search report for PCT/US96/14040 mailed Jan. 14, 1997.
International preliminary examination report for PCT/US96/14040 mailed Dec. 9, 1997, 6 pages.
Bahnemann, H.G., "Inactivation of Viruses in serum with Binary Ethyleneimine", Journal of Clinical Microbiology, vol. 3, No. 2, pp. 209–210 (1975).
Bahnemann, H.G., "Inactivation of Viral Antigens for Vaccine Preparation with Particular Reference to the Application of Binary Ethylenimine", Vaccine, 8:299–303 (1990).
Budowsky et al., "Inactivation of the phage MS2 infectivity by the action of ethyleneimines," Biorg. Khim. 11:989–991 (1985) (in Russian). English Abstract provided, 1 page.
Budowsky, E.I. and Zalesskaya, M.A., "Principles of selective inactivation of viral genome. v. Rational selection of conditions for inactivation of the viral suspension infectivity to a given extent by the action of B–propiolactone," Vaccine 9:319–325 (1991).
Budowsky, E.I. et al., "Principles of Selective Inactivation of the Viral Genome; Dependence of the Rate of Viral RNA Modification on the Number of Protonizable Groups in Ethyleneimine Oligomer", Vaccine Research, 5(1):29–39 (1996).
Dermer, O.C. and Ham, G.E. Ethyleneimine And Other Aziridines, Acad. Press, NY–London (1969), pp. 249–285.
Earley, J.E et al., "Reactions of Ethylenimines. IX. The Mechanisms of Ring Openings of Ethylenimines in Acidic Solutions," J. Am Chem. Soc. 80:3458–3462 (1958).
King, "Evaluation of Different Methods of Inactivation of Newcastle Disease Virus and Avian Influenza Virus in Egg Fluids and Serum," Avian Diseases 35:505–514 (1991).
Kochetkov, N.K. and Budowsky, E.I. eds., Organic Chemistry of Nucleic Acids, Part A, Plenum Press, London–New York, pp. 48–55, (1972).
Kostyanovskii et al., "Oligomers of azridines and N–beta–azridinoethylamides," Bulletin of Academy of Sciences of the USSR, Division of Chemical Science vol. 37(11):2315–2325, May 20, 1989. (Translated from IzvestiyaAkademi Nauk SSSR, Seriya Khimicheskaya 11:2566–2575).
Prodouz et al., "Inhibition of Merocyainine 540–mediated Photosensitization of Platelets and Viruses," Transfusion 31:415–422 (1991).
Race, E. et al., "An Experimental Chemically Inactivated HIV–1 Vaccine induces Antibodies that Neutralize Homologous and Heterologous Viruses", Vaccine, 13(1):.54–60 (1995).
Tanirbergenov, T.B. et al., "Regularities of mutagenic and toxic effects of ethyleneimine and its oligomers. A comparative study in the automated system SOS–chromotest and in standard bacterial test systems," Genetika 24:763 (1998) (in Russian). English translation provided, 5 pages.
Van Etten,, R.L. and Dolhum, J.J., "Effects of Hydrogen–Bond Formation by Phenols on the Conformational Equilibrium of trans–1, 2–Dimethyl–3–isopropylaziridine," J. Org. Chem. 33:3904–3907 (1968).
Wagner et al., "Approaches to the Reduction of Viral Infectivity in Cellular Blood Components and Single Donor Plasma," Transfusion Med. Rev. V:18–32 (1991).

Primary Examiner—Donna C. Wortman
Assistant Examiner—Brenda Brumback
Attorney, Agent, or Firm—Clark & Elbing LLP

[57] ABSTRACT

This invention provides means and methods of inactivating viruses and other organisms in cell-containing or biopolymer-containing compositions without significant alteration of proteins or other biopolymers by contacting such compositions with selective ethyleneimine oligomer inactivating agents, such as the trimer or tetramer.

17 Claims, 3 Drawing Sheets

METHODS FOR THE SELECTIVE MODIFICATION OF VIRAL NUCLEIC ACIDS

CROSS REFERENCE TO RELATED APPLICATIONS

This application is a continuation-in-part of application Ser. No. 08/05,045 filed Aug. 29, 1996, now abandoned, which in turn is a continuation-in-part of application Ser. No. 08/521,245 filed Aug. 29, 1995.

BACKGROUND OF THE INVENTION

This invention relates to the fields of bio-organic chemistry, molecular biology, biochemistry, immunology and virology and human and veterinary medicine. In particular, it relates to methods and compositions for selective chemical modification of nucleic acids contained in compositions such as human blood, blood cellular components, blood plasma and plasma biopolymers purified from blood (albumin, clotting factors, immune globulin, fibrinogen etc.), cell culture constituents such as fetal bovine serum and porcine trypsin, non-blood products produced from normal or cancerous cells (e.g., recombinant DNA technology) such that each is rendered essentially free of infective viral contaminants and remains suitable for therapeutic or diagnostic use. In particular this invention also relates to methods of inactivating viral, bacterial, and cellular genomes in the preparation of killed vaccines and other medical products.

Transmission of viral diseases (e.g., hepatitis A and B, acquired immunodeficiency syndrome (HIV), cytomegalovirus infections) by blood or blood products is a significant problem in medicine. While donor selection criteria and screening of donor blood for viral markers helps reduce the transmission of viruses to recipients, screening methods are incomplete or less than 100% sensitive, as most are directed only to a few discrete viruses, and even in that case their sensitivity is insufficient. It is desirable to inactivate any virus contained in donor blood or blood products without altering the structure and function of its valuable constituents, e.g., red blood cells, platelets, leukocytes, and plasma biopolymers, such as proteins, polysaccharides etc. Similarly, other biological compositions, e.g., mammalian and hybridoma cell lines, products of cell lines, milk, colostrum and sperm, can contain infectious virus and it would be advantageous to inactivate said virus(es) while retaining the valuable constituents or products of these compositions. Finally, it is often unknown whether blood or blood products, or products of mammalian cells, contain infectious viruses. In this case it would be valuable to have compositions and methods to treat such cell- or biopolymer-containing composition to inactivate any infectious viruses present.

The manufacture of maximally safe and effective killed vaccines for human or veterinary use requires methods which completely and reliably render live microorganisms, e.g., viruses and bacteria, noninfectious ("inactivated") but which have minimal effects on their immunogenicity. Methods typically used for the inactivation of viruses, such as those useful in the preparation of viral vaccines, generally alter or destroy the function and structure of cells, cell components, proteins and other antigens.

Current inactivation methods, including the use of formalin, beta-propiolactone and ultraviolet radiation, have been developed empirically, with little basis in fundamental chemical or structural principles. Ethyleneimine monomers have been used to inactivate the foot-and-mouth disease virus (Russian patent no. SU 1915956). Ethyleneimine monomers have also been used to inactivate Mycoplasma and Acholeplasma (WO 92/18161) and avian infections (Romania patent no. RO 101400). Binary ethyleneimine has been used for inactivation of feline enteric coronavirus, FECV, (EP 94200383). Polyethyleneimine has been used as a plant virus control agent (JP 7882735). The foregoing methods and compounds modify microorganisms, such as viruses and bacteria, nonspecifically, and are difficult to standardize and apply reproducibly. In general, multiple components of the microorganism, including important surface antigenic determinants, for example viral capsid proteins, are affected by currently used inactivating agents, which modify not only nucleic acids but also other biopolymers such as proteins, carbohydrates and lipids, impairing their function. Altered antigens or inactivation of protective epitopes can read to reduced immunogenicity and hence low potency (e.g., inactivated polio vaccine), to altered antigenicity and hence immunopotentiation of disease instead of disease prevention (e.g., respiratory syncytial virus and inactived measles vaccines produced by formalin inactivation) or to appearance of new antigens common to another killed vaccine prepared with the same inactivant. Another example is in the preparation of a hepatitis B virus vaccine, where it is common practice to heat the preparation at temperatures in excess of 80° C. and to treat with formaldehyde. These treatments not only inactivate viral infectivity, but also damage proteins and other antigens. Carrier substances added to the vaccine as stabilizers also may be unintentionally modified, producing allergic reactions, as occurs with human serum albumin in rabies vaccine inactivated with beta-propiolactone. In addition, ignorance of which chemical alterations render the microorganism noninfectious makes the process difficult to apply reproducibly. Periodic outbreaks of disease resulting from inadequate inactivation or reversion following inactivation are the result. Major outbreaks of paralytic poliomyelitis, foot and mouth disease and Venezuelan equine encephalitis have occurred due to this problem.

Hence none of the currently available agents used to produce inactivated viral vaccines are selective enough to completely inactivate infective viruses while preserving the antigenic properties of the virus particles, at least under conditions used so far for inactivation of the viral genome.

Yet another problem is that some of the viruses contaminating blood or other biological fluids are contained within the cell, either as a fully formed virus, viral genormle fragments or viral nucleic acid integrated into the host genome. For instance, the HIV virus is contained within leukocytes. It is a special concern to be able to inactivate both cell-free and cell-contained forms of virus, while retaining the structural integrity of cells.

The problems of inactivation of viruses in biological mixtures are distinct from the problems of inactivation of the viruses alone due to the co-presence of the desirable biopolymers such as proteins, carbohydrates, and glycoproteins in the plasma. While it is possible to inactivate the hepatitis B virus by using agents such as formaldehyde, or oxidizing agents, these methods are not suitable for the inactivation of the virus in blood due to the observation that most of these activating agents impair the biological activity of biopolymers in plasma or cellular components of blood. The use of ultraviolet light has been shown to inactivate viruses in a platelet concentrate. However, severe platelet damage resulted from higher doses. Beta-propiolactone reacts with nucleic acid and protein at similar rates; thus, while viruses can be inactivated, more than half of the factor VIII content of plasma is lost.

Problems may also exist in obtaining valuable biopolymers from non-blood sources since pathogenic viruses may also contaminate such compositions. These sources include, but are not limited to, mammalian colostrum and milk, ascitic fluid, serum, saliva, placental extracts, tissue culture cell lines and their extracts, including for example transformed cells, and products of fermentation.

It is an object of this invention to provide methods and compositions which allow selective modification of nucleic acid in the presence of other valuable biological macromolecules and cells. According to the methods and compositions of this invention, the nucleic acid of viruses, other microorganisms and cells, are selectively chemically modified, while preserving structure and function of non-nucleic acid components. It is also an object of the invention to provide selective inactivating agents to inactivate the virus, microorganism or cells while preserving their immunogenicity and achieving maximum reproducibility. It is another object of this invention to produce effective killed viral vaccines.

SUMMARY OF THE INVENTION

It has now been discovered that ethyleneimine oligomer inactivating agents can effectively and specifically inactivate viruses in a biological composition, such as a cell- or biopolymer-containing composition. This invention provides methods for selective modification of the nucleic acid molecules of viruses or other microorganisms in a composition of mixed biopolymers comprising contacting the composition with an ethyleneimine oligomer inactivating agent.

It has now been discovered that while most of the currently available viral inactivating agents alter biopolymers, such as the blood protein factor VIII, to render them biologically inactive, the ethyleneimine oligomer inactivating agents of this invention used under inactivating conditions, do not have this effect. It has been discovered that when a biopolymer-containing composition, e.g., blood cell proteins, blood plasma, a blood plasma fractionation precipitate, a blood plasma fractionation supernatant, cryoprecipitate, cryosupernatant, or portion or derivative thereof or serum or a non-blood product produced from normal or transformed cells (e.g. via recombinant DNA technology) is contacted for a sufficient period of time with an ethyleneimine oligomer inactivating agent, that viruses present in the composition are inactivated to the desired extent (at least about 6 logs by measuring viral inactivation or by at least about 20 logs by calculation) without significant damage to biopolymers such as proteins contained therein. By contacting a blood protein mixture or concentrate with an ethyleneimine oligomer inactivating agent, the virus, such as hepatitis A or B or HIV, can be inactivated to the desired extent, e.g., to a measurable degree of inactivation of greater than at least about 6 logs or by calculation to at least about 20 orders of magnitude. Biopolymers such as proteins, carbohydrates and lipids in a treated composition retain essentially all of their activity at pre-inactivation levels.

The inactivating agents and methods of this invention provide biopolymer-containing compositions, for example, blood cell derivatives (e.g., hemoglobin, alpha interferon, human growth hormone, erythropoietin, PDGF, tPA etc.) blood plasma, blood plasma fraction, blood plasma precipitate (e.g. cryoprecipitate, ethanol supernatant or polyethylene glycol supernatant), which are rendered essentially free of infectious virus while retaining essentially quantitatively the activity of the protein present before inactivation. The amount of virus in a composition is determined by infectivity titrations.

The process of the present invention has been described in terms of treatment of plasma, plasma fractions, plasma concentrates or components thereof. The process, however, is also useful in treating the lysates or proteins secreted by cells. Also contemplated are treatment of fractions derived from platelets, white cells (leukocytes), red cells, fibroblasts, and included are solutions of interferon, growth hormone, tPA, factor VIII, transfer factor, hemoglobin, growth factors, EPO and DNAse.

It is also contemplated using the inactivating agents and process of the present invention, that one can treat fresh frozen plasma, thawed frozen plasma, cryoprecipitate, cryosupernatants or concentrates from frozen plasma, as well as dilution products thereof.

By the same process described herein, virus present in products of normal or transformed cells can be inactivated while retaining biopolymer activity in such products. For example, using the ethyleneimine oligomer inactivating agent one can inactivate products produced using normal or transformed cells, the exudate from normal or transformed cells, hybridomas and products produced by genetic engineering. Such treatment does not substantially adversely affect the desired biopolymer such as a particular protein. Cells used for production of desired protein can, of course, be mammalian, as well as non-mammalian cells.

The methods and compositions of this invention inactivate substantially all of the viruses contained in a sample. Methods for determining infectivity levels are well known to one of ordinary skill in the art. See, e.g., Lennette, E. H. and Schmidt, N. J. (eds) (1985) *Diagnostic Procedures for Viral, Rickettsial and Chlamydial Infections*, 62nd ed, American Publisher's Assn., Wash., D.C. According to the invention, experimentally measurable inactivation of virus is obtained to the extent of at least about "6 logs," (6.0 $\log_{10}$). That is, where that virus is present in an untreated composition in such a concentration that even after dilution by a factor of $10^6$ viral infectivity can be detected, in the treated sample, virus is totally inactivated to the extent determined by infectivity studies, so that after treatment no virus is detectable in the undiluted material. More significantly, having obtained a precise kinetic description of the inactivating process as described herein, one can achieve a calculated reduction of the infectivity of virus-containing compositions of at least about 20 orders of magnitude.

In certain embodiments, the ethyleneimine oligomer inactivating agent is a trimer, linear tetramer or branched tetramer. Preferred inactivating conditions include incubating the composition with about 0.0001 M to about 0.010 M ethyleneimine oligomer inactivating agent; at about pH 6.5 to about pH 8.5; in a solution having an ionic strength of about 0.01 M to about 0.5 M. More preferred reaction conditions are incubating the composition with about 0.001 M to about 0.01 M ethyleneimine oligomer inactivating agent, at about pH 6.9 to about pH 8.5; in a solution having an ionic strength of about 0.1 to about less than about 0.5 M. The most preferred inactivating conditions is to contact the cell or biopolymer-containing compositions with an ethyleneimine oligomer inactivating agent such as the trimer, linear tetramer or branched tetramer at a temperature in the range of about 4° C. to 30° C.

This invention also provides inactivating agent compositions for selective modification of nucleic acids in a mixture of biopolymers comprising about 0.0001 M to about 0.015 M an ethyleneimine oligomer; having an ionic strength of about 0.1 M to about 0.2 M; at about pH 6.5 to about pH 8.5.

This invention further provides methods of selective inactivation of functional nucleic acids in a biological composition comprising contacting the composition with an effective concentration of a selective ethyleneimine oligomer inactivating agent.

This invention also is directed to methods of preparing a killed vaccine by contacting purified or nonpurified virus-containing compositions with a selective ethyleneimine oligomer inactivating agent under viral inactivating conditions.

In another embodiment, this invention provides killed vaccines having an effective amount of inactivated viruses, i.e., an amount sufficient to impart a desired degree of immunity on an organism, and a pharmaceutically acceptable carrier wherein the inactivated viruses are made by the process of incubating viruses with the ethyleneimine oligomer inactivating agents of this invention under viral inactivating conditions effective to reduce measurable infectivity by at least about 6.0 $\log_{10}$ (or to the desired extent of at least about 20 logs by calculation) such that the vaccine can be administered to a patient or animal for therapeutic purposes.

In a therapeutic method, this invention provides for immunizing a subject against a virus by administering to the subject a killed vaccine of this invention.

This invention also provides blood-collection devices comprising a container for receiving blood or a fraction thereof, the container comprising an ethyleneimine inactivating agent in an amount effective to inactivate viruses in blood or a fraction thereof received into the container.

In another embodiment this invention is directed to diagnostic reagents and diagnostic specimens which include viruses which have been treated with the viral inactivating agents of this invention under inactivating conditions.

DETAILED DESCRIPTION OF THE INVENTION

Figure 1:
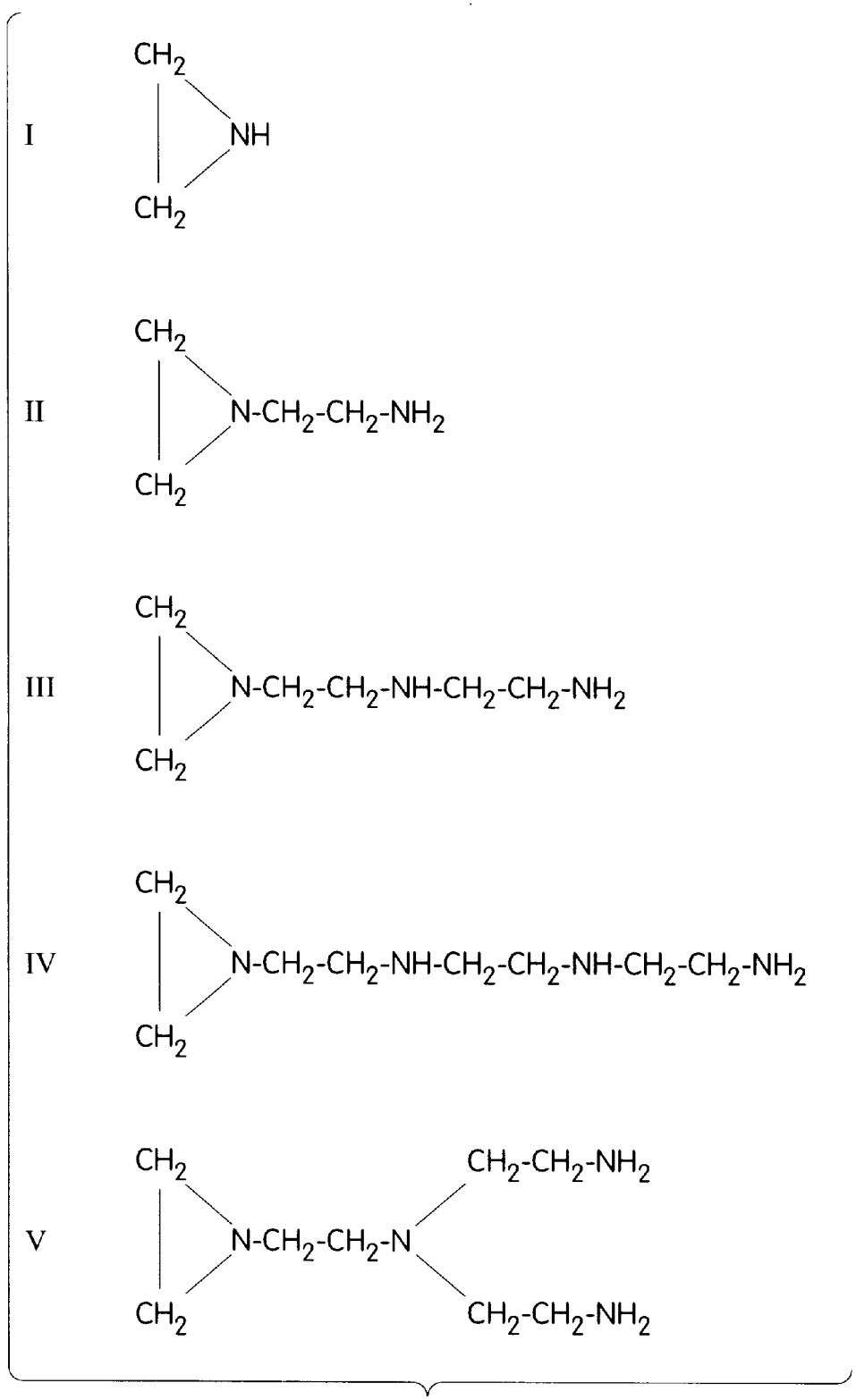
FIG. 1. Structure of monomer (I), dimer (II), trimer (III), linear and branched tetramers (IV and V, respectively) of ethyleneimine oligomer inactivating agent(s).

1. Definitions:

"Selective inactivating agents" refers to ethyleneimine oligomer reagents having an aziridino moiety and having specific affinity for polyanions, e.g., polynucleotides, over other biological molecules. The selective inactivating agents of this invention comprise a relatively low toxicity class of compounds, which selectively bind to the nucleic acids (single-stranded DNA, double-stranded DNA, or RNA) that comprise the genetic material of viruses and irreversibly modify the functional nucleic acids rendering the viruses inactive when used under inactivating conditions.

An "ethyleneimine oligomer" according to this invention refers to oligomers of ethyleneimine having a terminal aziridino group and optionally substituted. Preferred ethyleneimine oligomers of this invention have at least three ethyleneimine units and include, for example, the trimer or the tetramer, either linear or branched. Synthesis of the ethyleneimine oligomers of this invention is carried out using synthetic schemes well known to the ordinarily skilled artisan. See for example, Kostyanovskii, R. G. et al. (Translated from *Izvestiya Akademzi Nauk* SSSR, Seriya Khimicheskaya, 11:2566–2577, 1988.) Representative ethyleneimine oligomers are presented in FIG. 1. In the methods of this invention, ethyleneimine oligomers of less than ten units are preferable and ethyleneimine oligomers of about three or four units are more preferable.

Ethyleneimine oligomers also can be substituted so long as this does not eliminate the essential property of the ethyleneimine. II one embodiment, the ethyleneimine oligomers are substituted with halogens and have the general formula $\beta$-Hal-$(CH_2-CH_2-NH)_n$H. Preferably, "n" is an integer between 2–5, inclusive. Such compounds, often referred to as nitrogen mustards, are synthesized by the quantitative conversion by hydrogen chloride or hydrogen bromide of ethyleneimine or its oligomers into $\beta$-halogenomono- or oligoethylamines. The synthetic methods will be described in more detail below. The nitrogen mustards are strong electrophiles and alkylate nucleophilic groups of nucleic bases either directly or through intermediate conversion into the respective aziridines. As ethyleneimine oligomers, the $\beta$-halogenooligo-ethylamines have high affinity for polyanions. Therefore, these ethyleneimine oligomers have a high selectivity for nucleic acids, however the kinetics of modification will require adjustment.

An inactivating agent has "selectivity" for nucleic acids or "selectively" reacts with nucleic acids, if the comparative rate of reaction of the inactivating agent with nucleic acids is greater than the rate of reaction with other biological molecules, e.g., proteins, carbohydrates or lipids. The level of selectivity of ethyleneimine oligomer inactivating agent for nucleic acids over proteins is unexpected in view of ethyleneimine monomer, which is about as selective for nucleic acids as other alkylating agents.

"Nucleic acid" refers to both DNA and RNA both single and double stranded.

"Biological composition" means a composition containing cells or biopolymers. Cell-containing compositions including, for example, whole blood, red cell concentrates, platelet concentrates, leukocyte concentrates, blood cell proteins, blood plasma protein fractions, purified blood proteins, serum, semen, mammalian colostrum and milk, placental extracts, products of fermentation, ascites fluid, and products produced in cell culture by normal or transformed cells (e.g., via recombinant DNA or monoclonal antibody technology). "Biopolymer" or "biological molecule" means any class of organic molecule normally found in living organisms including, for example, nucleic acids, polypeptides, post-translationally modified proteins (e.g. glycoproteins), polysaccharides and lipids. Biopolymer-containing compositions include, for example, blood cell proteins, blood plasma, a blood plasma fractionation precipitate, a blood plasma fractionation supernatant, cryoprecipitate, cryosupernatant, or portion or derivative thereof or serum or a non-blood product produced from normal or transformed cells (e.g. via recombinant DNA technology). Biological compositions can be cell-free.

"Functional nucleic acid" means a nucleic acid having sequence elements that serve as template in replication, transcription, translation or other activity of the nucleic acid molecule. Such elements include, for example, sequences encoding the origin of replication of a nucleic acid molecule, transcriptional elements such as promoters/enhancers, transcriptional terminators and other regulatory elements; translational elements such as ribosome binding sites, translational start codons and coding sequences and in-phase stop codons; and sequences conferring RNA catalytic activities.

"Inhibit the activity of a biopolymer" means to measurably decrease the function or activity of the biopolymer. The decrease in function or activity can be determined by any standard assay used to measure the activity of the particular biopolymer. For example, the inhibition of an enzyme (protein) or antigen activity can be determined by measuring changes in the rate of an enzymatic process or an immune response to the antigen using conventional assays. Another example of such inhibition is the inhibition of translation of an RNA that can be determined by measuring the amount of protein encoded by the RNA that is produced in a suitable in vitro or in vivo translation system.

"Inactivating," "inactivation," or "inactivate" when referring to functional nucleic acids means to substantially eliminate the activity of DNA or RNA, for example, by destroying the ability to replicate, transcribe or translate a message. For example, the inhibition of translation of an RNA can be determined by measuring the amount of protein encoded by a definitive amount of RNA produced in a suitable in vitro or in vivo translation system. When referring to viruses, the term means diminishing or eliminating the number of infectious viral particles measured as a decrease in the infectious titer or number of infectious virus particles per ml. Such a decrease in infectious virus particles is determined by assays well known to the ordinarily skilled artisan. Lennette, E. H. and Schmidt, N. J. (eds) (1985) *Diagnostic Procedures for Viral, Rickettsial and Chlamydial Infections*, 62nd ed, American Publisher's Assn., Wash., D.C.

Experimentally, a decrease in infectivity can be measured to at least about "6 logs" in a cell- or biopolymer-containing composition wherein the virus is inactivated to the extent determined by infectivity studies where that virus is present in the untreated serum in such a concentration that even after dilution to $10^6$, viral activity can be measured. When a specific virus cannot be produced to a titer of $10^6$, inactivation is determined by direct quantitation measured up to the titer of virus produced. Alternatively, such a decrease in the number of infectious virus particles is determined by calculation as described herein to the extent of at least about "20 logs" based upon a kinetic description of the inactivation process based on a precise experimental determination of the infectivity of the viral suspension during inactivation while taking into account chemical, physical and biological factors affecting inactivation kinetics.

"Viral inactivating conditions" refers to the conditions under which the viral particles are incubated with the selective ethyleneimine oligomer inactivating agents of this invention, including, for example, time of treatment, pH, temperature, salt composition and concentration of selective inactivating agent so as to inactivate the viral genome to the desired extent. Viral inactivating conditions are selected from the conditions described below for selective modification of nucleic acids.

"Virus" means both DNA and RNA viruses. Viruses include both enveloped and non-enveloped viruses, for example, poxviruses, herpes viruses, adenoviruses, papovaviruses, parvoviruses, reoviruses, orbiviruses, picornavirus, rotaviruses, alphaviruses, rubiviruses, influenza virus, type A and B, flaviviruses, coronaviruses, paramyxoviruses, morbilliviruses, pneumoviruses, rhabdoviruses, lyssaviruses, orthomyxoviruses, bunyaviruses, phleboviruses, nairoviruses, hepadnaviruses, arenaviruses, retroviruses, enteroviruses, rhinoviruses and the filoviruses.

"Vaccine" is used in its ordinary sense to mean an agent effective to confer the necessary degree of immunity on an organism while causing only very low levels of morbidity or mortality. Methods of making vaccines are, of course, useful in the study of the immune system and in preventing animal or human disease.

"Pharmaceutically acceptable" means relatively non-toxic to the animal to whom the compound is administered. "Pharmaceutically acceptable carrier" encompasses any of the standard pharmaceutical carriers, buffers and excipients, such as a phosphate buffered saline solution, water, and emulsions, such as an oil/water or water/oil emulsion, and various types of wetting agents and/or adjuvants.

2. General:

This invention is based on the unexpected and surprising discovery that compared with many agents that modify nucleic acids and, in particular, with ethyleneimine monomer (aziridine), ethyleneimine oligomers, such as the trimer and tetramer forms, are significantly more selective in their modification of nucleic acids over other biopolymers, such as proteins. Ethyleneimine oligomers are more selective than ethyleneimine monomer by many orders of magnitude and, in some cases, six orders of magnitude. The use of the selective ethyleneimine oligomer inactivating agents in the methods of this invention is particularly effective with compositions comprising nucleic acids in close association with proteins, such as nucleoproteins or viruses.

This invention provides methods and conditions for selective amino-alkylation of nucleic acid molecules in a cell- or biopolymer-containing composition comprising contacting the composition with an ethyleneimine oligomer inactivating agent. As a result of the process, nucleic acids in the composition are chemically modified at rates much faster than the other biological molecules. The methods are useful in any process in which the practitioner wishes to modify nucleic acids but leave other biological molecules relatively unchanged. For example, the methods of this invention are useful in preferentially labeling nucleic acids in a nucleoprotein (e.g., chromatin or ribosomes) with ethyleneimine oligomer bearing a detectable label (radioactive, fluorescent, enzymatic, etc.), for example for mapping, or for inactivating the genome of a virus or other live organism.

Ethyleneimine oligomer inactivating agents of this invention modify nucleic acids preferentially through the reaction of the protonated aziridino group with nucleic bases in polynucleotides. The ability of the viral inactivating agent to associate with a polyanion depends, in part, upon the number of protonizable groups per molecule and upon the total degree of protonation under given conditions. Modification occurs through association of the oligocationic viral inactivating agent with the nucleic acid polyanion. Degree of protonation depends, in part, upon pH. As described herein, the pK of the aziridine group decreases with the length of the polymer. However, the ability of ethyleneimine oligomer inactivating agents to selectively associate with nucleic acids increases significantly with length of the ethyleneimine oligomer inactivating agent. Accordingly, the practitioner can effectively and selectively alkylate nucleic acids at physiological pH.

One embodiment of a method to selectively amino-alkylate nucleic acids involves the step of contacting the nucleic acids with about 0.0001 M to about 0.015 M of a selective ethyleneimine oligomer inactivating agent at about pH 6.5 to about pH 8.5 and, preferably, about pH 7.0 to about pH 8.0, and, most preferably, about pH 7.5. The concentration of the ethyleneimine oligomer inactivating agent depends in part on the number of protonizable groups in the ethyleneimine oligomer inactivating agent and the selection of the pH depends on the stability of the virion. The selective ethyleneimine oligomer inactivating agent is preferably an ethyleneimine, trimer, linear tetramer or branched tetramer. In another embodiment, the method includes the step of exposing or contacting the nucleic acids with selective ethyleneimine oligomer inactivating agents in a solution having an ionic strength of about 0.1 M to about 0.5 M and, preferably, about 0.15 M. The salts can be any of those normally used in biochemistry including sodium, potassium, phosphate or acetate and so forth. The practitioner can adjust the pH of the solution using many buffers customarily used in the art to handle biopolymers or cells, such as acetate, Tris, HEPES, MOPS and so forth. MOPS and Tris are preferred buffers. High concentrations of phosphate in buffers are not favored. The practitioner can adjust the reaction conditions to achieve the desired pH and ionic strength. The practitioner also can adjust other factors such as concentration of the reactants, temperature, time of incubation which depends on the reaction conditions and on the desired extent of infectivity inactivation. As described herein below, using a kinetic approach the inactivation end point should be determined as well as the conditions from among those described to amino alkylate nucleic acids to inactivate to a predetermined extent functional nucleic acids or viruses.

The practitioner can determine the extent of alkylation of a viral nucleic acid by the extent of viral infectivity inactivation, using various assays known to the ordinarily skilled artisan such as determination of cytopathic effect (CPE) in tissue culture using serial dilutions of virus-containing mixtures introduced into susceptible cells, followed by incubation at 37° C. Modification of proteins, polysaccharides and glycoproteins with ethyleneimine oligomers would lead to introduction of additional positive charges. The extent of this biopolymer modification can be determined by means known in the art including, for example, isoelectric focusing, polyacrylamide gel electrophoresis, HPLC and other forms of chromatography with detection by autoradiography or of the suitable method.

This invention is also directed to compositions for selective modification, amino alkylation, of nucleic acids in a cell- or biopolymer-containing composition comprising about 0.0001 M to about 0.015 M ethyleneimine oligomer inactivating agent; having an ionic strength of about 0.1 M to about 0.2 M and, preferably, about 0.15 M; and buffered at about pH 6.5 to about pH 8.5 and, preferably, about pH 7.0 to about pH 8.0, and, most preferably, about pH 7.5. The ethyleneimine oligomer inactivating agent is, preferably, a trimer or tetramer, either linear or branched. The salts and buffers can be any of those described above. In one embodiment, the composition has amounts of ethyleneimine oligomer, ionic strength and pH in amounts effective to amino-alkylate a functional nucleic acid. In another embodiment, the composition has concentrations of ethyleneimine oligomer, ionic strength and pH in amounts effective to inactivate viruses. These compositions are useful as disinfectants or as viricides, and in all the methods of the invention, described herein.

This invention is also directed to methods of selective inhibition of the activity of functional nucleic acids in a biological sample comprising contacting the sample with an effective amount of a selective ethyleneimine oligomer inactivating agent. These methods have many uses. When the functional nucleic acid is a naked nucleic acid, such as a plasmid or a DNA segment, inhibition is useful to decrease the ability of the molecule from transforming a cell into which it becomes incorporated by, for example, transfection. In a cell-free translation system, inhibition is useful to decrease translation of the RNA. When the functional nucleic acid is catalytic nucleic acid, such as a ribozyme, the methods are useful to inhibit the action of the nucleic acid on its target.

When the functional nucleic acid is a viral genome that is part of an infective virus, the methods are useful in disinfecting an area, inactivating or eliminating viruses from cell or biopolymer-containing compositions such as whole blood, blood products or biological products such as proteins made in cell culture, and to inactivate the infectivity of a virus to a desired extent (e.g. at least about 20 logs by calculation as described herein). The biopolymer-containing composition may include for example proteins purified from whole blood; blood products such as (e.g., clotting factors such as factor VIII, hormones such as erythropoietin and so forth); the products of cell culture, such as cell extracts, growth medium enriched with biological molecules (e.g. recombinant proteins); protein containing compositions processed with blood products (e.g., compositions incubated with calf serum) and plant products. These methods are useful helping to ensure the purity and safety of these products for use both in the laboratory and in therapy while retaining the critical biological properties of the biological product in the composition.

Similarly, if the functional nucleic acid is bacterial or is part of other organism's genome, the methods are useful in disinfecting or eliminating such bacteria or other organism.

Modifying the viral genome by the methods of this invention precludes reproduction of viruses and hence abolishes the infectivity of the killed vaccines of this invention. Furthermore, since the virion coat proteins are not modified to the same extent, the vaccine retains significant immunogenicity. Because ethyleneimine oligomers are significantly more selective in their modification of nucleic acids as compared with other selective inactivating agents, compositions of this invention comprising the ethyleneimine oligomers provide significant advantages over other inactivating agents currently in use which are less selective.

Accordingly, this invention is also directed to methods of preparing a killed vaccine comprising contacting a virus with a selective ethyleneimine oligomer inactivating agent under viral inactivating conditions. Viral inactivating conditions are selected from the methods described above for amino-alkylating and inactivating viral, bacterial or other organism's nucleic acids. In general, virus at a high titer of about $10^7$ to $10^8$ units per ml is incubated with ethyleneimine oligomer; at about pH 6.5 to about pH 8.5, in a solution having an ionic strength of about less than 0.50 M at about 4° C. to about 40° C. The time of treatment (i.e., end point of inactivation) depends on the structure and composition of the particular virus, temperature of incubation, ionic strength, and the number of protonizable groups in the ethyleneimine oligomers. However, kinetic studies indicate that depending on pH and the virus to be inactivated, incubation time could be as little as a few seconds, and also can be about 1 hour, 5 hours, 50 hours, 100 hours, 300 hours or 500 hours. Preferably, the selective ethyleneimine oligomer inactivating agent is a trimer, linear tetramer or branched tetramer. Methods of preparing vaccines are well known in the art and can be found, for example, in *Vaccines* (Slorein, G. Martance, E. eds) Second edition, 1994, Saunders, Harcourt-Brace, Phil, Toronto.

For vaccine use, the killed virus can be used directly in vaccine formulations, or lyophilized in individual or multiple dose containers for subsequent mixture with the pharmaceutically acceptable carrier. Lyophilized killed viruses usually are kept at 4° C.

The vaccine also can be administered in an adjuvant, i.e., a substance that potentiates an immune response when used in conjunction with an antigen. The vaccine can be given in an immunization dose. An immunization dose is an amount of an antigen or immunogen needed to produce or enhance an immune response. This amount will vary with the presence and effectiveness of various adjuvants. The amount will vary with the animal and immunogen or antigen or adjuvant but will generally be less than about 100 mg per dose. The immunization dose is easily determined by methods well known to those skilled in the art, such as by conducting statistically valid host animal immunization and challenge studies. See, for example, *Manual of Clinical Immunology*, H. R. Rose and H. Friedman, American Society for Microbiology, Wash., D.C. (1980).

Methods of treating cell- or biopolymer-containing compositions or preparing killed vaccines are particularly useful in the inactivation of viruses already known in the art to be irreversibly inactivated by other alkylating agents, such as ethyleneimine monomer and β-propiolactone. Therefore, while the agents of this invention have broader use by virtue of their selectivity, in selecting viruses for the preparation of vaccines or biological products for decontamination, the practitioner is guided, in part, by experience in the art with other inactivating agents.

This invention also is directed to a killed vaccine comprising an effective amount of inactivated viruses and a pharmaceutically acceptable carrier wherein the inactivated viruses are made by a process of treating viruses under viral inactivating conditions effective to diminish infectivity to a desired extent (to at least about 6 logs by direct measurement or to at least about 20 logs by calculation as described herein). The vaccines of this invention are useful in the prevention of animal or human disease. Vaccines capable of conferring the desired degree of immunity will, of course, contain an amount of inactivated virus effective to evoke an immune response. The viral genome in these vaccines as compared to other vaccines are alklated at the endocyclic nitrogen of the nucleic base but differ substantially by the fact that the inactivation is much more efficient because the relative rate of modification of nucleic acids over other biopolymers in the virion is significantly greater than can be achieved by any other selective inactivating agents. In the preparation of killed vaccines, the sample of virus is incubated with the selective inactivating agents of this invention in amounts and under such conditions to inactivate the virus while retaining immunogenicity.

Suitable pharmaceutical carriers and their formulations are described in Martin, *Remington's Pharmaceutical Sciences*, 19th Ed. (Mack Publishing Co., Easton 1995). Such compositions will, in general, contain an effective amount of the compound together with a suitable amount of carrier so as to prepare the proper dosage form for proper administration to the subject.

This invention is further directed to therapeutic methods of immunizing a subject against a virus by administering to the subject a killed vaccine of this invention. The subject can be a human or non-human animal. In the practice of the therapeutic methods of the present invention, an effective amount of a compound of this invention as described above, is administered via any of the usual and acceptable methods known in the art, either singly or in combination with another compound of the invention.

In the practice of the therapeutic methods of the invention, the particular dosage of the vaccine to be administered to the subject will depend on a variety of considerations including the nature of the virus, the schedule of administration, the age and physical characteristics of the subject, and so forth. Proper dosages may be established using clinical approaches familiar to the medicinal arts.

While not wishing to be limited by theory, the increased specificity of selective ethyleneimine oligomer inactivating agents for nucleic acids apparently involves the following factors that can be manipulated in the practice of this invention. Ethyleneimine monomer and ethyleneimine oligomers contain a single aziridino group (FIG. 1). The reactivity of aziridines as electrophilic agents increases dramatically with the protonation of the aziridine nitrogen (Van Etten, R. L. and Dolhun, J. J. (1968) *J. Org. Chem.* 33:3904–3913), but is only slightly affected by its alkylation (Earley, J. E. et al. (1958) *J. Am Chem. Soc.* 80:3458–3462). Therefore, the form of these compounds protonated at aziridino group probably is the only reactive form. The rates of usual electrophilic reactions of aziridines should be proportional to the concentration of their protonated forms in the solution.

Compounds I to V of FIG. 1 differ significantly from each other in the $pK_a$ of their aziridino groups and in the number, mutual arrangement, and $pK_a$ of the amino groups (Table 1). Therefore, both the fraction of the reactive form of these compounds, in which the aziridino group is protonated, and their total average positive charge depend significantly on pH (Table 2).

TABLE 1

| $pK_a$ values of protonizable groups of oligoethyleneimines | | | | |
|---|---|---|---|---|
| | aziridino | primary amino | secondary amino | tertiary amino |
| monomer (I) | 8.10 | — | — | — |
| trimer (III) | 4.10 | 10.0 | 7.35 | — |
| tetramer (IV) (linear) | 3.3 | 10.0 | 7.05* | — |
| tetramer (V) (branched) | 3.0 | 10.0 | — | 6.4 |

*mean value for two secondary amino groups
**mean value for two primary amino groups The action of aziridines on proteins and polynucleotides leads to arnino-alkylation of nucleophilic groups in both amino acid residues and nucleic bases (Dermer, O. C. and Ham, G. E. (1969) *Ethyleneimine And Other Azriidines*, Acad. Press, NY—London 52:249–285). Aziridines, like many electrophilic agents, modify nucleic acids preferentially at N7, N3, and N1 of purines and to a much lesser extent at N3 of pyrimidines (Hemminki, K. and Ludlum, D. B. (1981) *J. Natl. Cancer Inst.* 73:1021–1027; Musser, S. M. et al. (1992) *Chem. Res. Toxicol.* 5:95–99; Singer, B. and Grunberger, D. (1983) *Molecular Biology of Mutagens and Carcinogens*, Plenum Press, New York-London; Loveless, A. (1966) *Genetic and Allied Effects of Alkylating Agents*. Butterworths, London; and Kochetkov, N. K. and Budowsky, E. I. eds. (1972) *Organic Chemistry of Nucleic Acids*, Part B, Plenum Press, London-N.Y.). Template synthesis is arrested by alkylating agents primarily due to relatively slow opening of imidazole ring of N7 alkylated purines, predominantly of guanine (O'Connor, T. R. et al. (1988) *Nucl. Acids Res.* 16:5879–93; Hemminki, K. (1984) *Chem.-Biol. Interactions.* 48:249–260). For example, ethyleneimine modifies guanosine to produce N7(aminoethyl)-guanosine which displays a much higher rate of imidazole ring opening than does N7-alkylguanosine (Hemminki, K. (1984) *Chem.-Biol. Interactions.* 48:249–260; Hemminki, K. el al. (1989) *Chem.-Biol. Interactions.* 70:289–303).

TABLE 2

Total average positive charge of the oligoethyleneimines (A) and the extent of their aziridino group protonation (B)

| pH values | A 6.5 | 7.5 | 8.5 | B 6.5 | 7.5 | 8.5 |
|---|---|---|---|---|---|---|
| monomer (I) | 0.96 | 0.80 | 0.28 | 0.98 | 0.80 | 0.28 |
| trimer (III) | 1.88 | 1.41 | 1.04 | $4.0 \cdot 10^{-3}$ | $4.0 \cdot 10^{-4}$ | $4.0 \cdot 10^{-5}$ |
| tetramer (IV) (linear) | 2.67 | 1.41 | 1.01 | $6.3 \cdot 10^{-4}$ | $6.3 \cdot 10^{-5}$ | $6.3 \cdot 10^{-6}$ |
| tetramer (V) (branched) | 2.44 | 2.07 | 1.98 | $3.2 \cdot 10^{-4}$ | $3.2 \cdot 10^{-5}$ | $3.2 \cdot 10^{-6}$ |

The transition from the ethyleneimine monomer (I) to its tetramers (IV and V) at pH 7.5 produces an increase of more than two orders of magnitude in the effective rate constant of phage infectivity inactivation (k), calculated based on the average concentration of the agent in solution (Table 3). Such a transition leads to a decrease of five orders of magnitude in the $pK_a$ value of the aziridino group. Accordingly, the fraction of the reactive form of the agent decreases at this pH by about four orders of magnitude (Table 2). Thus, the transition from monomer to tetramers at pH 7.5 leads to an increase by about six orders of magnitude of the rate constant, calculated based on the average concentration of the reactive form of the agent in solution ($k_1$).

TABLE 3

Rate constants of the phage MS2 infectivity inactivation ($M^{-1} \cdot min^{-1}$) by the action of oligoethyleneimines in 0.15 M NaCl at 20° C. calculated basing on the total average concentration of the reactive form of the agent ($k_1$, in parenthesis)

| pH values | 6.5 | 6.9 | 7.5 | 8.5 |
|---|---|---|---|---|
| monomer (I) | — | — | 1.5 ± 0.07 (1.25) | — |
| dimer (II) | 102 ± 3* ($2.4 \cdot 10^{3)}$ | 35 ± 2.3 ($2.0 \cdot 10^3$) | 13 ± 1.4 ($2.9 \cdot 10^3$) | 1.7 ± 0.05 ($3.8 \cdot 10^3$) |
| trimer (III) | — | — | 47 ± 2.7 ($1.5 \cdot 10^5$) | — |
| tetramer** | — | — | 150 ± 12.5 ($3.6 \cdot 10^6$) | — |

*rate constant was calculated using the initial part of the survival curve.
**equimolar mixture of linear and branched tetramers.

As oligocations, ethyleneimine oligomers have high affinity for polynucleotides, reflected in their association constant. This association constant, influenced by electrostatic interaction, is proportional to the oligocation and polyanion volume charge densities and therefore increases with the total average positive charge of the oligocation. The transition from ethyleneimine monomer to its oligomers leads to a marked increase in the total average positive charge of the molecule (Table 2). In addition, the distances between protonizable groups in the ethyleneimine oligomers are comparable with the distance between internucleotide phosphate groups in polynucleotides. An increase in the number of protonizable groups in oligoethyleneimines upon monomer to tetramer transition should therefore lead to an increase in their association with polynucleotides, for example with viral RNA (Manning, G. S. (1978) *Q. Rev. Biophys.* 2:179–246; Thomas, T. J. and Bloomfield, V. A. (1984) *Biopolymers* 23:1295–1306; and Stevens, L. S. (1967) *Biochem. J.* 103:811–815).

Many alkylating agents used for nucleic acid modification have no marked affinity for polynucleotides. Comparison of the pH-dependence of polynucleotide modification with the pK values of nucleic bases shows that in the pH range 6.0–8.0, it is primarily the neutral forms of the nucleic bases that are alkylated (Budowsky, E. I. and Zalesskaya, M. A. (1991) *Vaccine,* 9:319–325; Singer, B. and Grunberger, D. (1983) *Molecular Biology of Mutagens and Carcinogens,* Plenum Press, New York-London; Loveless, A. (1966) *Genetic and Allied Effects of Alkylating Agents,* Butterworths, London; and Kochetkov, N. K. and Budowsky, E. I. eds. (1972) *Organic Chemistry of Nucleic Acids,* Part B, Plenum Press, London-New York) 48, 50, 51). Further increase in pH should lead to increase in a fraction of more reactive deprotonated forms of guanosine and uridine, and, hence, to the increase in the phage inactivation rate. However, the rate constant of the phage infectivity inactivation at pH 8.5 is less than at pH 7.5 (Table 3). Hence, at least in this pH range, the influence of the fraction of reactive form of the agent on the inactivation rate is more than that of nucleic bases. Therefore, in calculating the infectivity inactivation rate constant in pH range 6.0–8.5, we assume that the fraction of nucleic bases in their reactive (deprotonated) form is essentially constant. For oligoethyleneimine inactivation of phage MS2, then, the pH-dependence of the inactivation rate constant is due mainly to the fraction of the reactive form and total average positive charge of the inactivating agent.

There is a 60-fold increase in the effective inactivation rate constant caused by the decrease in pH from 8.5 to 6.5. This correlates with the increase in the reactive fraction of this agent in the solution (Tables 2 and 3). So in this case the effect of pH on the inactivation rate is determined mainly by change in concentration of the reactive form in solution. It should be emphasized, however, that the pH-dependence of the total average positive charge for trimer and tetramers is much more pronounced than for ethyleneimine monomer (Table 1), leading to a greater variation in the rate of polynucleotide modification with trimer and tetramers compared to monomers and dimers.

The rate of modification of any of the virion components by traditional inactivating agents is usually considered a function of the average solution concentration of the agent. If a low-molecular-mass agent has a specific affinity for some polymer, however, the local concentration of agent near this polymer is higher than the average solution concentration of the agent and exponentially decreases with increased distance from the polymer (Dolar, D. and Peterlin, A., (1969) *J. Chem. Phys.,* 50:3011–3015). The selectivity of viral genome inactivation should be proportional to the difference in the local concentration of the agent near these biopolymers. Therefore, even a local increase in oligoethyleneimine concentration near the genome should preferentially increase its modification rate. However, as considered above, the formation of complexes between oligomers of ethyleneirnine and polynucleotides should increase the extent of aziridino group protonation, and, hence, the rate constant ($k_1$) of polynucleotide modification. Because of the exponential decrease in agent concentration with distance, at 1–2 nm away from the polymer the local concentration of agent is essentially the same as its average solution concentration (Dolar, D. and Peterlin, A., (1969) *J. Chem. Phys.,* 50:3011–3015). Obviously, the fraction of the reagent reactive form at this distance should be the same as in the free (non-associated) state in solution. Therefore, the inactivating agent's concentration increase in the vicinity of polynucleotide, as well as association of the inactivating agent with polynucleotide, should not affect the modification rate of capsid component, especially their antigen-bearing regions at the surface of the virion. The selectivity of the viral genome inactivation is enhanced by the use of the selective ethyleneimine oligomer inactivating agents of this invention possessing specific affinity for nucleic acids compared to traditional inactivating agents.

All these data and considerations allow one to select an ethyleneimine trimer or tetramer, with accompanying increase in polynucleotide affinity, with an increased rate of reaction and selectivity of the viral genome modification. As presented above, such a transition leads to an increase in selectivity by at least six orders of magnitude. Thus, even if the selectivity of the ethyleneimine monomer is no better than the selectivity of other agents used now for preparation of whole virion killed vaccines, the significant increase in selectivity of the trimer and tetramer makes negligible the effect of virion component modification on immunogenicity, stability and other virion properties.

The use of the selective ethyleneimine oligomer inactivating agents with selectivity for polynucleotide modification provides new opportunities for preparation of safe and efficient killed antiviral vaccines. The same approach may also be used for selective inactivation of viruses which are the most harmful contaminants in donors' blood and serum, as well as in medical and veterinary preparations isolated from animal tissues and cell cultures. The same approach may be used for selective inactivation of biologically active (e.g. transforming) DNA fragments, which may contaminate the cell- or biopolymer-containing compositions.

The following examples are offered by way of illustration, not by way of limitation.

Preparation Of Halogen Salts

As is mentioned above, the oligoethyleneaniine viral inhibitors of the invention can be provided in the form of hydrohalide salts; the preferred halogens are chlorine, bromine, and fluorine.

Preparation of β-Chloro-Oligoethyleneamine Hydrochlorides

These chloride salts have the formula β-chloro-($CH_2$—$CH_2$—NH)$_n$H, wherein n is an integer between 2 and 5, inclusive. The most preferred oligomeric salts have either 3 or 4 of the repeating unit (Cl—$CH_2$—$CH_2$—NH). The formula for the trimer chloride salt can be expressed as: [Cl—$CH_2$—$CH_2$—NH—$CH_2$—$CH_2$—NH—$CH_2$—$CH_2$—$NH_2$](HCl)$_3$. The tetramer chloride salt can be expressed as: [Cl—$CH_2$—$CH_2$—NH—$CH_2$—$CH_2$—NH—$CH_2$—$CH_2$—NH—$CH_2$—$CH_2$—$NH_2$](HCl)$_4$.

The chloride salts are prepared as follows:

1. Add dropwise (preferably through a cooled capillary) 0.6–0.7 mmole (about 100 μl) of oligoethyleneimine trimer or tetramer over 3–5 minutes to 0.8 ml of vigorously stirred and cooled (0° C.) concentrated HCl. Continue stirring for an additional 10 min.

2. Pour out the reaction mixture into 40 ml of absolute ethanol, stir, and keep at −20° C. for 1–2 hours.

3. Filter the reaction mixture through a porous glass filter under water pump-generated vacuum and wash resulting crystals three times with 15 ml of absolute ethanol. Recrystallize from aqueous ethanol. Dry at 50° C. The result is white crystals, perfectly soluble in water and almost insoluble in cold ethanol.

4. TLC analysis: ascending on silica gel plates on aluminum foil. Solvent system: freshly (1–2 hours before use) prepared mixture of monomethyl ether of ethyleneglycolpropionic acid/$H_2O$ (14:3:3 v/v), saturated with NaCl. Develop for approximately 40 minutes (solvent front migration of about 7 cm). Stain with ninhydrin according to conventional procedure.

| Compound | Mr | Tm (C.) | $R_1$ Value |
|---|---|---|---|
| β-chloro-ethyleneamine trimer hydrochloride | 275 | 200 | 0.86 |
| β-chloro-ethyleneamine tetramer hydrochloride | 364.5 | 216 | 0.80 |

The trimer bromide salt is prepared as follows:

Place 0.79 ml of 48% hydrobromic acid (6.6 mmol) in a glass vessel with a wide neck (capacity=5 ml) supplied with magnetic stirring bar and cool vessel to 0° C. in water bath with vigorous stirring. Place 100 mg of ethyleneimine trimer (0.78 mmol) in a glass tube with a capillary end and cool it to 0° C. Then dip the capillary end of the tube into cooled stirred hydrobromic acid and begin slow (during >1 min) addition of ethyleneimine trimer. Upon addition of trimer the yellowish color of hydrobromic acid solution disappears. Following completion of addition, continue stirring for 20 min. more at 0° C. and then bring the mixture to room temperature. Place the open vessel into a vacuum dessicator with sufficient amount (about 300 g) of solid alkali and gradually reduce the pressure by an oil pump. Dry the mixture in a dessicator until complete evaporation of liquid (10–12 hours).

Dissolve the solid remainder (white crystalline mass) in about 20 ml of boiling ethanol, and remove the solid remnants by filtering through a hot glass filter. Maintain the filtrate for about 24 hours at −20° C. Filter the solid tribromide of N1-(β-bromoethyl)-diethylenetriamine through the glass filter, wash with cold ethanol (3×3 ml) and dry at 25° C. Yield of the dry compound is 140 mg (40%). The resulting white non-hygroscopic crystals are readily soluble in water, poorly soluble in cold ethanol and insoluble in ether. Tm=176–177° (without decomposition). According to NMR (data not included), the compound is almost pure (more than 90%). An additional=120 mg of this compound with the same melting point may be obtained by slow addition of ether at room temperature to stirred mother solution until the appearance of white suspension. Place at 4° C. overnight, then filter, wash, and dry the crystals as described above. The total yield of N1-(β-Bromoethyl)-diethylenetriamine is ≈260 mg (75%).

EXAMPLE 1

Bacteriophage Inactivation Kinetic Determination

Bacteriophage MS2 was prepared according to conventional procedure. Purification was performed by polyethylene glycol (PEG 6000, Serva) resedimentation or by chromatography on DEAE-Sephadex A25 in a linear gradient of NaCl(0.02–1.0 M, 20 mM Tris HCl, pH 7.4). Purified phage was suspended in 0.15 M NaCl solution (2–10 ∥l per ml) and stored at +4° C. The infectivity of the virus suspension was determined by a conventional bilayer technique on a meat-peptone agar with *Escherichia coli* CA180.

Ethyleneimine (I), its trimer (III), and linear (IV) and branched (V) tetramers were prepared according to the method of Kostyanovsky et al. (1988) *Izv. Akad. Nauk SSSR* 11:2566–2575. The PMR data evidenced that the purity of these compounds was more than 95%. Solutions of ethyleneimines were prepared immediately before use by addition of the calculated volume of the compound (specific densities at 20° C. are 0.836, 0.945, and 0.968 g.cm$^3$ for compounds I, III, and IV (V), respectively) to 0.15 M NaCl solution.

Figure 2:
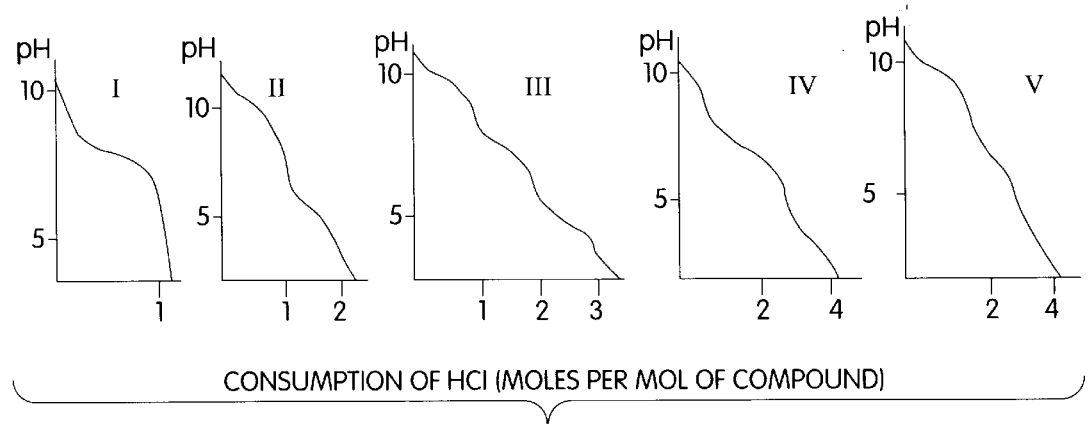
FIG. 2. Potentiometric titration curves of ethyleneimine and its oligomers. Roman numerals correspond to the structures present in FIG. 1.

The pK$_a$ values of the protonizable groups of ethyleneimines in 0.15 M NaCl aqueous solution at 25° C. were calculated basing on the results of the potentiometric titration (FIG. 2) by HCl using autotitrator TTT-60 (Radiometer) with a thermostatted cell compartment. The accuracy of the pK$_a$ value determination is no less than 0.05. The fraction of the reactive (protonized at the aziridine nitrogen) form of the agent (Q) was calculated by the following equation:

$$Q = \frac{1}{1 + 10^{pH-pK_i}} \quad (1)$$

where pK$_i$ is the pK$_a$ value of the aziridino group in the respective compound.

The total average positive charge of the molecule (p) was calculated using the following equation:

$$p = \sum_0^n n \cdot d \cdot (H_n \cdot A^{n+}) \quad (2)$$

where d. (H$_n$. A$^{n+}$) is the fraction of the agent having positive charge n at the given pH value.

Figure 3:
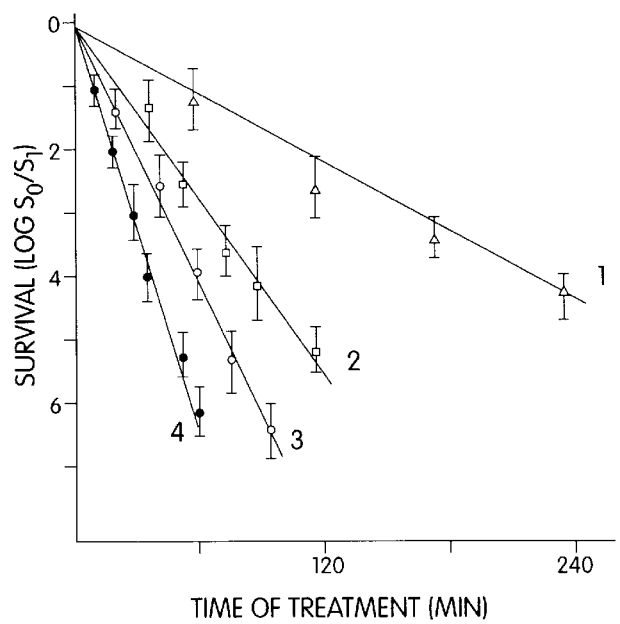
FIG. 3. Phage MS2 survival curves under the action of ethyleneimine (0.025 M, curve 1), its dimer (0.007 M, curve 2), trimer (0.003 M, curve 3), and equimolar mixture of linear and branched tetramers (0.0015 M, curve 4) in 0.15 M NaCl, pH 7.5, 20° C.

Before mixing, the phage-containing composition and freshly prepared solution of the selective ethyleneimine oligomer inactivating agent were kept at 20° C. and the desired pH was adjusted by addition of dilute NaOH or HCl solutions. Aliquots of the reaction mixture incubated at 20° C. (final concentrations of the inactivating agent are given in the brief description of FIGS. 3 and 4) were taken at defined time intervals and after immediate 100-fold dilution used for the determination of the infectivity (titer). The effective rate constants of infectivity inactivation (k) were calculated by the following equation:

$$k = \frac{2.3}{A \cdot t} \log S_o / S_t \quad (3)$$

where A is the concentration (total or of the reactive fraction) of the agent; S$_o$ and S$_t$ are the infectivity (titer) of the suspension before and t min after the start of inactivation.

The well-defined shapes of the potentiometric titration curves (FIG. 2) reflect alterations in the ionic status of the ethyleneimine oligomer inactivating agent. In the case of the monomer, the single plateau corresponds to protonation of the aziridino group. The calculated pK$_a$ value (Table 1) is in a good agreement with the literature data (O'Rourke, C. E., et al., (1956) *J. Am. Chem. Soc.*, 78:2159–2160. For other compounds, the plateaus correspond to the protonation of amino and aziridino groups (Table 1). Consumption of acid by the oligomers II to V indicates that each has a single group with pK$_a$ 5.15–3.0, which corresponds to the presence of a single aziridino group in these molecules. Molecules II to V demonstrate a decreased aziridino pK$_a$ relative to ethyleneimine because the greater number of strongly basic amino groups increases the total positive charge of the molecule, thereby decreasing protonation of aziridino groups. The less pronounced pK$_a$ difference between molecules IV and V is most probably due to the difference in the mutual arrangement of aziridino and amino groups in these molecules. One equivalent of acid is required for protonation of the most basic amino groups in the case of compounds II to IV, while two are. required for compound V. These data correlate with the presence of one primary amino group in each of the first three compounds, and two such groups in V. Consumption of one and two equivalents of acid, corresponding to the existence of one and two secondary amino groups, is necessary for ionic transitions of compounds III and IV at pH 7.35 and 7.05, respectively.

Consumption of one equivalent of acid for ionic transition of compound V at pH 6.4 corresponds to the existence of one tertiary amino group. In these compounds the higher pK$_a$ values of the primary versus secondary and tertiary amino groups are most probably due to electronic effects as well as the structure of the polyamine molecule (cf. M. D. Bratek-Wiewiorowsak et al. (1986) *Bull. Pol. Ac. Sci., Chem.* 34:229–249). These data were used to calculate the total average positive charge and extent of the aziridino group protonation at any pH value for compounds I to V (Table 2).

The exponential decrease in phage MS2 infectivity by the action of compounds I to V at pH 7.5 (FIG. 3) indicates that the concentration of these compounds remains constant under the conditions used. This allows calculation of the effective rate constants (k) for infectivity inactivation based on the data obtained. As shown in Table 3, the transition from ethyleneimine monomer to its tetramer leads to an increase by two orders of magnitude in this rate constant.

Figure 4:
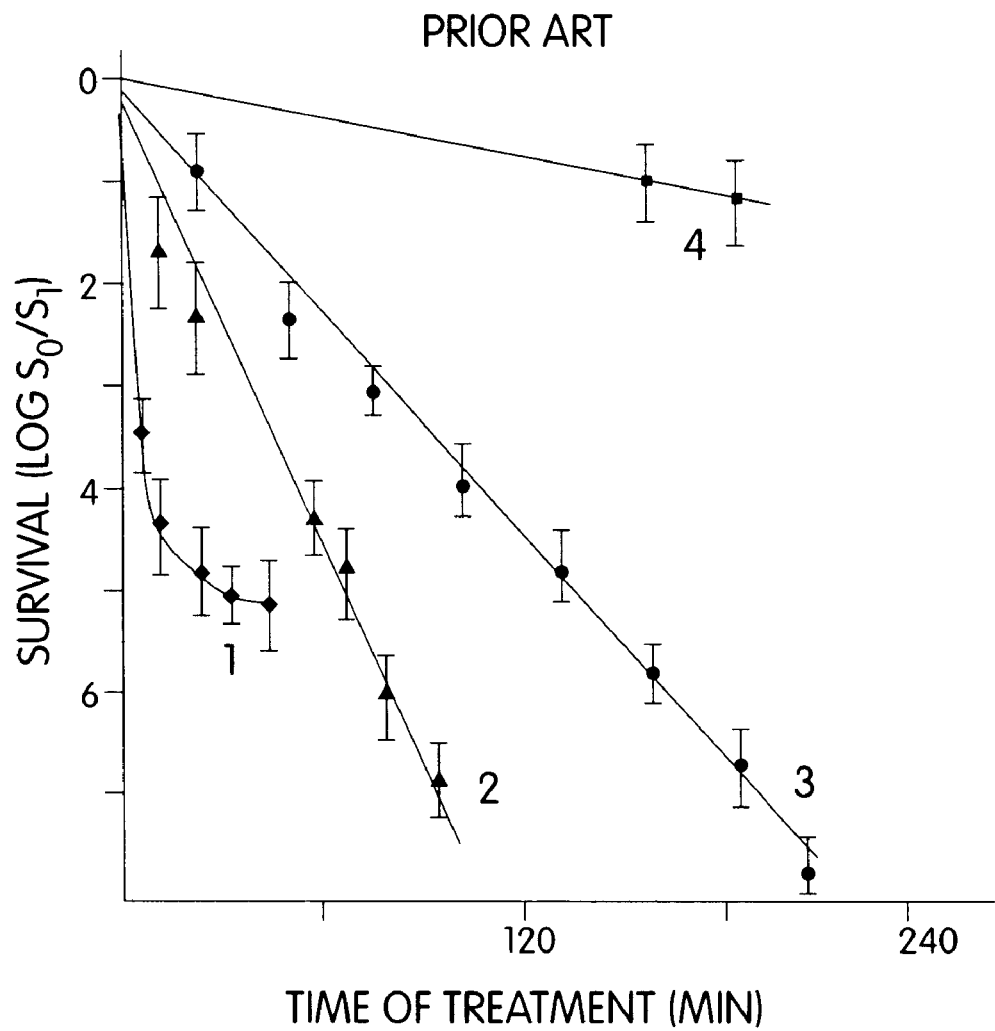
FIG. 4. Prior art diagram showing phage MS2 survival curves under the action of 0.007 M ethyleneimine dimer in 0.15 M NaCl (20° C.) at pH 6.5, 6.9, 7.5, and 8.5 (curves 1, 2, 3, and 4, respectively).

The decrease in pH from 8.5 to 6.5 causes a 60-fold increase in the rate of the phage infectivity inactivation by the ethyleneimine dimer (FIG. 4, Table 3). The use of this compound at pH 6.5 leads to a significant deviation of the survival curve shape from the exponential one (FIG. 4). This change indicates a rapid decrease in concentration of compound II most likely to its cationic polymerization at this pH (cf. Gembitsky, P. A., et al., (1791) *Nauka, Moscow*). The inactivation rate constant for compound II at pH 6.5 was therefore calculated using only the initial part of the survival curve. The rate constant for compound II consumption at pH 6.5 is about 0.02 min$^{-1}$, as calculated using the rate constant at the early period of inactivation and the ultimate extent of the infectivity inactivation (cf. Budowski, E. I. and Zalesskaya, M. A., (1991) *Vaccine*, 9:319–325).

EXAMPLE 2

Calculation of Inactivation Endpoint

The extent of infectivity reduction of the virus-containing composition may be controlled experimentally by at least about 6 orders of magnitude even if one increases the sample volume (within reasonable limits) and takes advantage of a series of successive passages. However, the production of safe killed antiviral vaccines requires that the infectivity of the original virus-containing composition be reduced by at least about 20 orders of magnitude. Therefore, in general, the safety of killed antiviral vaccines, cannot be determined solely by experiment and must be built into the method described herein and can be assessed more meaningfully by calculation using a kinetic approach. This requires an accurate kinetic description of the inactivation conditions for the virus taking into account characteristics of the selective inactivating agent of this invention. Data can be obtained from the early (experimentally controlled) part of the survival curve.

An accurate kinetic description should be based on a precise determination of the infectivity of the viral suspension during inactivation. The skilled artisan should assure that the infectivity (titer) determination be accurate to assure determination of the inactivation rate constant and the minimal duration of the selective inactivating agent action (t$_1$). A reliable value of t$_1$ can be obtained using the kinetic approach described above, particularly when the survival curves provide a good kinetic description up to a specified degree of reduction in infectivity. Assuming the modification of the viral genome is not distorted by biological factors (such as DNA repair) and assuming that the formation of the first inactivating lesion, regardless of its position in the viral nucleic acid, blocks the complete replication of the genome, the survival curves for the virus during the action of the selective inactivating agent of this invention obey the following equation:

$$S = S_0 \exp(-Akt)$$

where $S_0$ and $S$ are the infection titers of the virus-containing composition before and at time t after the start of the selective inactivating agent's action, A is the concentration of the selective inactivating agent and k is the rate constant for inactivation, i.e., modification of a nucleotide residue per genome.

Assuming the values of A and k are constant during inactivation, the survival curves are exponential. In this case, the inactivation duration required for a reduction of infectivity to a given extent can be calculated according to the following equation:

$$t_1 = [2.3/(Ak)] \log(S/S_0)$$

Applying the rate constant for inactivation obtained in Example One as set forth in Table 3, the inactivation duration, assuming the concentration of the ethyleneimine oligomer is $10^{-3}$ M (for the tetramer) and the rate constant of inactivation, k=150, taken from the Table 3 (H 7.5) and log $(S/S_0)$ is the desired extent of inactivation, in this case at least about 20, then the time for reduction of infectivity in example one is 15.3 minutes carried out at 20° C.

According to this invention, the endpoint of inactivation for any virus and any selective inactivating agent of this invention can be determined under inactivating conditions based on the data obtained from the initial part of the survival curve.

EXAMPLE 3

Picornavirus. Hepatitis A virus (genus enterovirus) and foot and mouth virus (aphthovirus) containing single-stranded RNA, positive chain, capsid containing only protein viruses are studied. The viruses are prepared according to conventional procedures including purification and determination of infectivity and stability. The selective ethyleneimine oligomer inactivating agent of this invention is prepared as described above. The pKa values of the ethyleneimines in a particular salt solution and at a particular temperature are determined. The virus and the selected viral inactivating agent, i.e., the ethyleneimine oligomer, is mixed at a particular pH, temperature and concentration using the conditions for each of the viruses as set forth in Table 4.

TABLE 4

The time for inactivation of some animal viruses infectivity (15–20 orders of magnitude) - by the action of ethyleneimine tetramer at 20° C.

| virus | stability under conditions of treatment | Time of incubation hours* Concentration of the agent | | | |
|---|---|---|---|---|---|
| | | 1 mM | | 15 mM | |
| | | pH 7.0 | pH 8.0 | pH 7.2 | pH 8.0 |
| Vesicular stomatis virus | reasonable | 120 | 1200 | | |
| Influenza A virus | reasonable | 1–50 | 10–300 | 0.07–0.2 | 0.7–2 |
| Hepatitis A virus | stable | 1–30 | 10–300 | 0.15–0.3 | 1.5–3 |
| Foot-and-Mouth Disease virus | reasonable | 2–5 | 20–500 | 0.15–0.3 | 1.5–3 |

*depends on the type and strain of the virus, method of the virus purification, and composition of the reaction mixture Samples of the reaction mixture taken at appropriate time intervals were supplemented by thiosulfate (final concentration 0.1 M) for 30 minutes to quench the excess of the inactivating agent, and the infectivity titer of the reaction mixture is measured as described above. The time $t_1$ for reduction of these viruses infectivity by 20 orders of magnitude is calculated using the equation described above. For example, applying the rate constant for inactivation is approximately 500 (which is known to one of ordinary skill and is based on a comparison of the length of the genome of Hepatitis A as compared to the bacteriophage MS2 as described in example one), the inactivation duration, assuming the concentration of the ethyleneimine oligomer is $10^{-4}$ M (for the tetramer) and the rate constant of inactivation, k=500 (pH 7.5) and log $(S/S_0)$ is the desired extent of inactivation, in this case at least about 20, then the time for reduction of infectivity in this example is 30 minutes carried out at 20° C.

EXAMPLE 4

Rhabdoviruses. The inactivation of vesicular stomatitis virus (VSV) containing single-stranded RNA virus and a lipid-enveloped nucleocapsid is studied.

VSV is cultured in human A549 cells. EMC stocks is prepared are mouse L929 or human A459 cells. Culturing and assay procedures are known to the ordinarily skilled artisan. Infectivity of VSV is assessed by endpoint, 10-fold serial dilutions in DMEM culture with 10% fetal calf serum. Each dilution is used to inoculate eight replicate wells of human A549 cells in 96 well microtiter plates. Virus induced cytopathology is scored after 72 hours of incubation at 37° C., in 5% $CO_2$. The reported virus titer is scored using known methods.

Cell-associated VSV is prepared by incubating a confluent monolayer of human A549 cells with 5ml of $10^7$ $ID_{50}$/ml VSV in serum-free DMEM for 1 hour at 37° C., under 5% $CO_2$ in 150 $cm^2$ tissue culture flasks. The multiplicity of infection under these conditions is approximately 2.1 $TCID_{50}$/cell. To assess inactivation, the selective ethyleneimine oligomer inactivating agent is added to the cell-associated virus in DMEM in 3 ml aliquots in polystyrene tubes. Aliquots of the reaction mixture are taken at definite time intervals and are supplemented with thiosulfate (final concentration 0.1 M) for 30 minutes to quench the excess of the selective inactivating agent. Cells are removed by centrifugation and the infectivity titer of the supernatant and redispersed pellet is evaluated. The time $t_1$ for reduction of these viruses infectivity by 20 orders of magnitude is calculated using the equation described above.

The inactivation of cell free VSV added to whole blood ($5 \times 10^9$ red blood cells/ml) in the presence of selective ethyleneimine oligomer inactivating agent is assessed. Virus infectivity is assessed as described herein. The time $t_1$ for reduction of these viruses infectivity by 20 orders of magnitude is calculated using the equation described above. Red blood cell structure and function is evaluated.

EXAMPLE 5

Orthomyxoviridae. The inactivation of influenza A virus a single stranded fragmented RNA, negative chain, lipid enveloped capsid virus is evaluated. The virus is prepared according to conventional procedures including purification and determination of infectivity and stability. The selective ethyleneimine oligomer inactivating agent of this invention is prepared as described above. The pKa values of the ethyleneimine oligomer in a particular salt solution and at a particular temperature are determined. The influenza A virus and the selected viral inactivating agent, i.e., the ethyleneimine oligomer, is mixed at a particular pH, temperature and concentration using the conditions for the virus as set forth above. Virus infectivity is assessed as described herein. The time $t_1$ for reduction of these viruses infectivity by a calculated 20 orders of magnitude is calculated using the equation described above.

EXAMPLE 6

Human immunodeficiency virus (two copies of a single-stranded RNA genome, frequently mutated capsid proteins) is studied. HIV in either a cell-free or intracellular form is added to either whole blood or a red cell concentrate in a test tube. The selective ethyleneimine oligomer inactivating agent is added and after processing of the samples HIV antigen measurements are made. Virus infectivity is assessed as described herein. The time $t_1$ for reduction of these viruses infectivity by a calculated 20 orders of magnitude is calculated using the equation described above.

From the foregoing description, it will be realized that the selective ethyleneimine oligomer inactivating agents and methods of this invention can be used to inactivate blood-transmitted viruses, bacteria, or parasites in cell- or biopolymer-containing compositions in various contexts, e.g., in the hospital, laboratory, as part of a kit. Since cell compositions also comprise a variety of proteins, the method of viral inactivation described herein is also applicable to protein fractions, particularly blood plasma protein fractions or purified blood products, including, but not limited to, fractions containing clotting factors (such as factor VIII and factor IX), serum albumin and/or immune globulins. The viral and bacterial inactivation may be accomplished by treating a protein fraction or purified protein with a selective ethyleneimine oligomer inactivating agent as described herein.

The process of the invention can be combined with still other modes of inactivating viruses. For example, certain processes used in the preparation of medical products (e.g. chromatography in buffers of low pH, or storage of red blood cells in acidic solutions containing calcium chelating agents) may have incidental viral inactivating properties for selected, sensitive viruses, usually enveloped viruses. Use of ethyleneimines would be additive with such agents in inactivation of such viruses.

EXAMPLE 7

Independence of reaction rate from surrounding protein concentration

The inactivation of MS2 phage was determined in the absence and presence of protein concentrations up to 3% (30 mg/ml) to determine whether high protein concentration in the media would significantly affect the rate of the reaction with the viral genome. MS2 phage suspended in 0.15 M NaCl was added to an equal volume of human serum albumin. Oligoethyleneimine trimer or tetramer was added to the phage suspensions to final concentrations of 0.4 mM or 0.2 mM respectively and incubated at pH 7.0, 25° C. Periodically, samples were removed and analyzed for residual infectivity (phage titer). The calculated rate constants are shown in Table 5:

TABLE 5

Rate constants for inactivation of phage MS-2 infectivity in the presence of human serum albumin

| Inactivation by Oligoethyleneimine trimer (0.4 mM) | | Inactivation by Oligoethyleneimine tetramer (0.2 mM) | |
| --- | --- | --- | --- |
| Albumin concentration (mg/ml) | Rate constant $(mM^{-1}h^{-1})$ + SE | Albumin concentration (mg/ml) | Rate constant $(mM^{-1}h^{-1})$ + SE |
| 0 | 10.8 ± 1.1 | 0 | 22.5 ± 4.2 |
| 10 | 9.8 ± 0.3 | 1 | 19.9 ± 2.2 |
| 20 | 10.4 ± 0.3 | 2 | 18.6 ± 1.8 |

The lack of appreciable effect of high protein concentrations on the rate of virus inactivation supports the high degree of selectivity of the reaction of ethyleneimines with the viral genome and confirms that nucleic acid modification can be achieved in biological or other fluids containing high concentrations of protein or other biopolymers.

EXAMPLE 8

Specificity of inactivation of phase infectivity (modification of nucleic acid): lack of modification of protein by ethyleneimine oligomers Inactivation of MS2 phage infectivity by ethyleneimine monomer (25 mM), trimer (0.4 mM) and tetramer (0.2 mM) was carried out in the presence of 0.9% human serum albumin to various degrees of inactivation in 0.02 M phosphate buffer, pH 7.0–7.2, at 25° C. Following termination of the inactivation reaction with thiosulfate (0.1 M final concentration), samples from each incubation were compared by 12.5% reducing and non-reducing SDS-PAGE and by isoelectric focusing (pH range 3 to 7).

As shown in Table 6, neither reduced nor non-reduced SDS-PAGE detected any difference in albumin following inactivation of up to 80 orders of magnitude, indicating a lack of appreciable effect of inactivation on the size of the protein.

TABLE 6

Absence of protein modification by ethyleneimine oligomers, SDS-page analysis

| Inactivation by monomer (25 mM) | | Inactivation by trimer (0.4 mM) | | Inactivation by tetramer (0.2 mM) | |
| --- | --- | --- | --- | --- | --- |
| Extent of inactivation ($log_{10}$) | SDS-PAGE | Extent of inactivation ($log_{10}$) | SDS-PAGE | Extent of inactivation ($log_{10}$) | SDS-PAGE |
| 0 | Baseline | 0 | Baseline | 0 | Baseline |

TABLE 6-continued

Absence of protein modification by ethyleneimine oligomers, SDS-page analysis

| Inactivation by monomer (25 mM) | | Inactivation by trimer (0.4 mM) | | Inactivation by tetramer (0.2 mM) | |
|---|---|---|---|---|---|
| Extent of inactivation ($\log_{10}$) | SDS-PAGE pattern[#] | Extent of inactivation ($\log_{10}$) | SDS-PAGE pattern[#] | Extent of inactivation ($\log_{10}$) | SDS-PAGE pattern[#] |
| 11 | No change* | 11 | No change* | 9 | No change* |
| 32 | No change* | — | — | — | — |
| 41 | No change* | 40 | No change* | 40 | No change* |
| 83 | No change* | 79 | No change* | 81 | No change* |

[#]For reduced and non-reduced SDS-PAGE, predominant major band at approximately 68 kDa with approximately 5 faint higher molecular weight bands.
*No change in either reduced or non-reduced SDS-PAGE However, as shown in Table 7, analysis of the albumin samples by isoelectric focusing (IEF) showed that inactivation with ethyleneimine monomer, but no trimer or tetramer, produced a significant increase in charge heterogeneity in the albumin, rendering it more basic. This indicates that ethyleneimine monomer modified the albumin, altering its charge. In contrast, ethyleneimine trimer and tetramer, for the same degree of inactivation, up to 81 orders of magnitude, had no detectable effect on albumin charge. This indicates that the inactivation reaction, with ethyleneimine oligomers is highly selective for nucleic acid, whereas inactivation with ethyleneimine monomer under the same conditions modifies proteins as well as nucleic acids.

TABLE 7

Absence of Protein Modification by Ethyleneimine Oligomers, isoelectric focusing analysis

| Inactivation by monomer (25 mM) | | Inactivation by trimer (0.4 mM) | | Inactivation by tetramer (0.2 mM) | |
|---|---|---|---|---|---|
| Extent of inactivation ($\log_{10}$) | IEF pattern | Extent of inactivation ($\log_{10}$) | IEF pattern | Extent of inactivation ($\log_{10}$) | IEF pattern |
| 0 | Baseline pattern[#] | 0 | Baseline pattern[#] | 0 | Baseline pattern[#] |
| 11 | Increase band width* | 11 | No change* | 9 | No change* |
| 32 | Increase band width* | — | — | — | — |
| 41 | Increase band width* | 40 | No change* | 40 | No change* |
| 83 | Increase band width* | 79 | No change* | 81 | No change* |

[#]Single major band at pI approximately 5.5.
*Increased width and diffuseness of major band, predominantly in the direction of increased positive charge (more basic).

EXAMPLE 9

Inactivation of an enveloped animal virus

To demonstrate inactivation of an enveloped animal virus, Venezuelan Equine Encephalitis virus ("VE") was incubated with ethyleneimine trimer (2 mM) or tetramer (0.5 mM) for up to 24 hours at 22 or 37° C. in 0.02 M phosphate buffer containing 2% bovine serum albumin. Samples were periodically removed from the incubation mixture and titered for residual virus concentration. Inactivation rate constants were determined from the data through the first 7 hours. Results are shown in Table 8 below:

TABLE 8

Rate constants for inactivation of venezuelan equine encephalitis virus by ethyleneimine - oligomers

| Temperature (° C.) | Rate constant for inactivation by oligoethyleneimine trimer ($mM^{-1}hr^{-1}$) | Rate constant for inactivation by oligoethyleneimine tetramer ($mM^{-1}hr^{-1}$) |
|---|---|---|
| 25 | 0.33 | 1.64 |
| 37 | 1.25 | 3.40 |

EXAMPLE 10

Preservation of antigenic epitopes during inactivation of an enveloped animal virus To demonstrate the preservation of antigenic epitopes during inactivation with ethyleneimine oligomers, Venezuelan Equine Encephalitis virus was inactivated for up to 7 hours by ethyleneimine trimer, 2 mM at 37° C. Antigenicity of the virus after three and seven hours of inactivation was performed by ELISA assay using three different monoclonal antibodies. Endpoint titers were determined and compared to titers of virus prior to inactivation. Monoclonal antibodies used were 1A1B-9, 7A1A-1, and 7A3A-4. Antibody 1A1B-9 recognizes a type-specific antigen, while antibodies 7A1A-1 and 7A3A-4 recognize a cryptic epitope which is exposed following unfolding of a viral capsid antigen.

As shown in Table 9, no change in antigenic reactivity was detected after inactivation of over 8 orders of magnitude (three hours of inactivations) or after an estimated 18.7 orders of magnitude (seven hours of inactivation).

TABLE 9

Preservation of antigenic epitopes during inactivation of venezuelan equine encephalitis virus by ethyleneimine trimer (2 Mm)

| | Time of incubation (hours) | | |
|---|---|---|---|
| | 0 | 3 | 7 |
| Virus titer | $2 \times 10^8$ | 0 | 0 |
| Endpoint, Antibody 1A1B-9 | $10^{-5}$ | $10^{-5}$ | $10^{-5}$ |
| Endpoint, Antibody 7A1A-1 | $10^{-3}$ | $10^{-3}$ | $10^{-3}$ |
| Endpoint, Antibody 7A3A-4 | $10^{-2}$ | $10^{-2}$ | $10^{-2}$ |

EXAMPLE 11

Kinetics of inactivation of MS2 phage with bromide salts of ethyleneamine oligomers To determine the kinetics of inactivation of MS2 phage with bromide salts of ethyleneamine oligomers, phage was incubated at 25° C. for various times up to 24 hours in one of several buffers at pH 7.0 together with ethyleneimine trimer, ethyleneimine tetramer, the hydrobromide salt of ethyleneimine trimer ($\beta$-bromoethyl-diethylenetriamine tribromohydrate) or the hydrobromide salt of ethyleneimine tetramer ($\beta$-bromoethyl-triethylenetetramine tetrabromohydrate). Samples were periodically removed for determination of residual infectivity, and rate constants for inactivation of infectivity were determined. Results shown in Table 10 indicate that MS2 phage was inactivated when incubated with the bromide salts by conversion into the respective trimer or tetramer of ethyleneimine. The somewhat slower rate of inactivation of the bromide salts compared to inactivation in the presence of the corresponding ethyleneimine oligomers indicates that the conversion was only approximately 30–40% complete. Nevertheless, use of halogen salts may be preferable due to their greater stability and convenience. The data also illustrate that phosphate anion inhibits the reaction, presumably on the basis of the high negative charge of phosphate anion or polyphosphate interfering with interaction of the ethyleneimine oligomers with nucleic acid.

TABLE 10

Inactivation rate constants of MS2 phage with ethyleneimine trimer and tetramer and the corresponding bromide salts

| | Rate constant (mM 'hr') | | | |
|---|---|---|---|---|
| Buffer | Ethyleneimine trimer | Ethyleneimine tetramer | ($\beta$-bromoethyl-diethylenetriamine tribromohydrate) | ($\beta$-bromoethyl-triethylenetetramine tetrabromohydrate) |
| A | 7.4 ± 0.6 | — | — | — |
| B | 7.6 ± 0.8 | 18.2 ± 1.6 | 3.0 ± 0.4 | 6.3 ± 0.9 |
| C | 5.1 ± 0.8 | 8.7 ± 0.9 | — | — |
| D | 0.26 ± 0.03 | 0.32 ± 0.04 | 0.17 ± 0.02 | 0.29 ± 0.04 |

A: 0.15 M NaCl
B: 0.075 M NaCl. 0.2 M MOPS
C: 0.1 M NaCl, 0.025 M phosphate
D: 0.075 M NaCl, 0.2 M phosphate Although described in connection with viruses, it will be understood that the methods of the present invention are generally also useful to inactivate any biological contaminant found in stored blood or blood products, including bacteria and blood-transmitted parasites.

Although the foregoing invention has been described in detail for purposes of clarity of understanding, it will be obvious that certain modifications may be practiced within the scope of the appended claims.

All publications and patent documents cited in this application are incorporated by reference in their entirety for all purposes to the same extent as if each individual publication or patent document were so individually denoted.

What is claimed is:

1. A method of inactivating an infectious animal virus in a biological composition containing non-viral protein, said method comprising contacting the composition with a selective ethyleneimine oligomer inactivating agent under viral inactivating conditions, wherein the biological composition is selected from the group consisting of human milk, human saliva, human semen, human serum, a human product of a mammalian cell culture, a human product of a non-mammalian cell culture, a human non-blood product produced by recombinant DNA technology, and a human placental extract.

2. A method of inactivate infectious animal viruses in a biological composition containing non-viral protein, said method comprising contacting the composition with a selective ethyleneirnine oligomer inactivating agent under viral inactivating conditions, wherein the biological composition is selected from the group consisting of red blood cell. concentrates, platelet concentrates, and leukocyte concentrates.

3. A method of inactivating infectious viruses in a biological composition comprising contacting the composition with a selective ethyleneimine oligomer inactivating agent under viral inactivating conditions, wherein the biological composition comprises one or more human purified protein selected from the group consisting of fibrinogen, factor VII, factor VIII, factor IX, factor X, immunoglobin, prealbumin, retinol-binding protein, albumi, alpha-globulins, gammaglobulins, complement components, fibronectin, antitbrombin III, hemoglobin, interferon, growth factors, plasminogen activator, growth hormone, insulin and elropoiefim.

4. A method of inactivating an infectious virus in a biological composition, wherein said virus is contained in a cell, said method comprising contacting the cell with a selective ethyleneimine oligomer inactivating agent.

5. A method of inactivating infectious animal viruses in a biological composition containing non-viral protein, said method comprising contacting the composition with a selective ethyleneimine oligomer inactivating agent under viral inactivating conditions, wherein said biological composition is selected from the group consisting of whole human blood, purified or partially purified blood proteins, purified or partially purified blood plasma, platelet-rich plasma, a plasma concentrate, a precipitate from any fractionation of said plasma, a supernatant from any fractionation of said plasma, and a blood cryoprecipitate.

6. The method of claim 1, 2, 3, 4, or 5, wherein the virus is selected from the group consisting of poxviruses, herpes viruses, adenoviruses, papovirus, parvoviruses, reovirases, orbiviruses, rotaviruses, alphaviruses, rubivinuses, flaviviruses coronavirses parimyoxviruses, morbillivirusesmse, pneumaviruses vesiculoviruses, lyssaviruses, picomaviuses, orthomyoxviruses, bunyaviruses, phleboviruses, nairoviruses, hepadnaviruses, arenaviruses, retroviruses, and filoviruses.

7. The method of claim 1, 2, 3, 4, or 5, wherein the step of contacting comprises incubating the biological composition with 0.0001 M to 0.015 M ethyleneimine oligomer; at pH 6.5 to pH 8.5; it a solution having an ionic strength of 0.1 M to 0.2 M at 15° C. to 3° C. for 1 hour to 500 hours.

8. The method of claim 7, wherein the step of contacting involves incubating the composition with 0.007 M ethyleneimine oligomer; at pH 7.0 to pH 8.0; in a solution having an ionic strength of 0.15 M.

9. The method of claim 1, 2, 3, 4, or 5, wherein the virus is an enveloped virus.

10. The method of claim 1, 2, 3, 4, or 5, wherein the virus is a non-enveloped virus.

11. The method of claim 1, 2, 3, or 5, wherein the virus is a non-enveloped virus and the ethyleneimine oligomer is ethyleneimine dimer or trimer.

12. The method of claim 11, wherein said ethyleneimine oligomer is ethyleneimine dimer.

13. The method of claim 2, wherein the biological composition is a red blood cell concentrate.

14. The method of claim 5, wherein said biological composition is whole human blood.

15. The method of claim 14, wherein said ethyleneimine oligomer is ethyleneimine dimer.

16. The method of claim 5, wherein said biological composition is human blood plasma.

17. The method of claim 16, wherein said ethyleneimine oligomer is ethyleneimine dimer.

* * * * *

UNITED STATES PATENT AND TRADEMARK OFFICE
CERTIFICATE OF CORRECTION

PATENT NO.    : 6,136,586
DATED         : October 24, 2000
INVENTOR(S)   : Edward I. Budowsky et al.

It is certified that error appears in the above-identified patent and that said Letters Patent is hereby corrected as shown below:

<u>Title page,</u>
OTHER PUBLICATIONS, Bahnemann reference, last line, change "1975" to -- (1976) --;

OTHER PUBLICATIONS, Kostyanovskii reference, second line, change "beta-aridinoethylamides" to -- beta-aziridinoethylamides; and change "Bulletin of Academy" to -- Bulletin of the Academy --;

<u>Column 1,</u>
Line 6, change "Ser. No. 08/05,045" to -- Ser. No. 08/705,045 --;

<u>Column 2,</u>
Line 16, change "read" to -- lead --;
Line 46, change "genormle" to -- genome --;

<u>Column 6,</u>
Line 16, change "Il" to -- In --;

<u>Column 11,</u>
Line 40, change "alklated" to -- alkylated --;

<u>Column 12,</u>
Line 46, change "arnino" to -- amino --;
Line 48, change "Azriidines" to -- Aziridines --;

<u>Column 14,</u>
Line 56, change "ethyleneirnine" to -- ethyleneimine --;

<u>Column 15,</u>
Line 32, change "oligoethyleneaniine" to -- oligoethyleneamine --;
Line 64, change "ethyleneglycolpropionic acid" to -- ethyleneglycol/propionic acid --;

<u>Column 16,</u>
Line 54, change "(2-10 ‖ 1per ml)" to -- 2-10 mg per ml) --;
Line 65, change "g.cm$^3$" to -- g/cm$^3$ --;

UNITED STATES PATENT AND TRADEMARK OFFICE
CERTIFICATE OF CORRECTION

PATENT NO. : 6,136,586
DATED : October 24, 2000
INVENTOR(S) : Edward I. Budowsky et al.

It is certified that error appears in the above-identified patent and that said Letters Patent is hereby corrected as shown below:

Column 17,
Line 61, change "are. required" to -- are required --;

Column 19,
Line 19, change "(H 7.5)" to -- (pH 7.5) --;

Column 20,
Line 22, change "stocks is" to -- stocks --;

Column 25,
Line 28, change "2 Mm" to -- 2 mM --;

Column 26,
Line 44, change "inactivate" to -- inactivating --;
Line 47, change "ethyleneirnine" to -- ethyleneimine --;
Line 49, change "cell." to -- cell --;
Line 56, change "protein" to -- proteins --;
Line 58, change "immunoglobin" to -- immunoglobulins --
Line 59, change "albumi" to -- albumin --;
Line 61, change "antitbromin" to -- antithrombin --;
Line 63, change "elropoiefim" to -- erythropoietin --;

Column 27,
Line 6, change "human" to -- mammalian --;
Line 14, change "papovirus" to -- papovaviruses --;
Line 14, change "reovirases" to -- reoviruses --;
Line 15, change "rubivinuses" to -- rubiviruses --;
Line 16, change "coronavirses" to -- coronaviruses --;
Line 16, change "parimyoxviruses" to -- paramyoxviruses --;
Line 16, change "morbillivirusesmse" to -- morbilliviruses --;
Line 17, change "pneumaviruses" to -- pneumoviruses --;
Line 17, change "picomaviuses" to -- picoraviruses --;
Line 18, change "phlebovirases" to -- phleboviruses --;
Line 24, change "it" to -- in --;

UNITED STATES PATENT AND TRADEMARK OFFICE
CERTIFICATE OF CORRECTION

PATENT NO. : 6,136,586
DATED : October 24, 2000
INVENTOR(S) : Edward I. Budowsky et al.

It is certified that error appears in the above-identified patent and that said Letters Patent is hereby corrected as shown below:

<u>Column 27, (cont.)</u>
Line 25, change "3º C" to -- 30º C --.

Signed and Sealed this

Eighteenth Day of June, 2002

Attest:

JAMES E. ROGAN
Attesting Officer  *Director of the United States Patent and Trademark Office*

UNITED STATES PATENT AND TRADEMARK OFFICE
Certificate

Patent No. 6,136,586                          Patented: October 24, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Edward I. Budowsky, Boston, MA; and Samuel K. Ackerman, Weston, MA.

Signed and Sealed this First Day of February 2005.

BRENDA BRUMBACK
*Supervisory Patent Examiner*
Art Unit 1642